(12) United States Patent
Pote et al.

(10) Patent No.: US 7,764,303 B2
(45) Date of Patent: Jul. 27, 2010

(54) IMAGING APPARATUS AND METHODS FOR CAPTURING AND ANALYZING DIGITAL IMAGES OF THE SKIN

(75) Inventors: Jeffrey Pote, Easton, PA (US); Gregory Payonk, Flanders, NJ (US); Nikiforos Kollias, Skillman, NJ (US); Dick Jackson, Victoria (CA); Eduardo Ruvolo, Plainsboro, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 296 days.

(21) Appl. No.: 11/863,342

(22) Filed: Sep. 28, 2007

(65) Prior Publication Data

US 2008/0079843 A1    Apr. 3, 2008

Related U.S. Application Data

(60) Provisional application No. 60/848,765, filed on Oct. 2, 2006.

(51) Int. Cl.
  *H04N 7/18*  (2006.01)
  *H04N 5/232* (2006.01)
  *A61B 6/00*  (2006.01)

(52) U.S. Cl. .................. 348/77; 348/211.3; 348/373; 600/477

(58) Field of Classification Search .............. 396/2; 348/77, 78, 373, 376, 211.3, 211.11; 600/476, 600/306, 477
See application file for complete search history.

(56) References Cited

U.S. PATENT DOCUMENTS

| | | |
|---|---|---|
| 2,005,426 A | 6/1935 | Land |
| 3,353,884 A | 11/1967 | Chaffee et al. |
| 3,904,293 A | 9/1975 | Gee |
| 3,971,065 A | 7/1976 | Bayer |

(Continued)

FOREIGN PATENT DOCUMENTS

EP    0682236    11/1995

(Continued)

OTHER PUBLICATIONS

"Apparatus and Method for Measuring Photodamage to Skin", U.S. Appl. No. 11/863,328, filed Sep. 28, 2007, Inventors: Gregory Payonk, et al.

(Continued)

*Primary Examiner*—Jason Whipkey
(74) *Attorney, Agent, or Firm*—Paul F. Swift (57) ABSTRACT

An imaging station for taking a plurality of digital images of a subject under a plurality of illuminating conditions and storing and analyzing the digital images, includes a housing, containing the digital image capturing apparatus, like a camera or video recorder, a computer for processing the image data and one or more displays for displaying images of the person. The imaging station aids in controlling lighting during image capture and may be used to optimally position the subject for imaging. The computer may be programmed to conduct various image processing functions and may be networked to allow image sharing. A display which may be provided on the exterior of the housing allows an operator to visualize the subject and to control the imaging process. The imaging station may be used for teaching purposes.

16 Claims, 4 Drawing Sheets

U.S. PATENT DOCUMENTS

| | | |
|---|---|---|
| 4,070,096 A | 1/1978 | Jasgur |
| 4,170,987 A | 10/1979 | Anselmo et al. |
| 4,398,541 A | 8/1983 | Pugliese |
| 4,592,726 A | 6/1986 | Brilliant |
| 4,842,523 A | 6/1989 | Bourdier |
| 4,905,700 A | 3/1990 | Wokalek et al. |
| 4,911,544 A | 3/1990 | Walsh |
| 5,005,975 A | 4/1991 | Kawai et al. |
| 5,016,173 A | 5/1991 | Kenet et al. |
| 5,198,875 A | 3/1993 | Bazin et al. |
| 5,241,468 A | 8/1993 | Kenet |
| 5,363,854 A | 11/1994 | Martens et al. |
| 5,446,515 A * | 8/1995 | Wolfe et al. .................... 396/2 |
| 5,456,260 A | 10/1995 | Kollias et al. |
| 5,539,540 A | 7/1996 | Spaulding et al. |
| 5,556,612 A | 9/1996 | Anderson et al. |
| 5,640,957 A | 6/1997 | Kaminski |
| 5,742,392 A | 4/1998 | Anderson et al. |
| 5,760,407 A | 6/1998 | Margosiak et al. |
| 5,785,960 A | 7/1998 | Rigg et al. |
| 5,836,872 A | 11/1998 | Kenet et al. |
| 5,945,112 A | 8/1999 | Flynn et al. |
| 5,973,779 A | 10/1999 | Ansari et al. |
| 5,991,433 A | 11/1999 | Osanai et al. |
| 6,018,586 A | 1/2000 | Kamei |
| 6,021,344 A | 2/2000 | Lui et al. |
| 6,032,071 A | 2/2000 | Binder |
| 6,076,904 A | 6/2000 | Shepherd et al. |
| 6,081,612 A | 6/2000 | Gutkowicz-Kruisn et al. |
| 6,134,011 A | 10/2000 | Klein et al. |
| 6,148,092 A | 11/2000 | Qian |
| 6,208,749 B1 | 3/2001 | Gutkowicz-Krusin et al. |
| 6,215,893 B1 | 4/2001 | Leshem et al. |
| 6,251,070 B1 | 6/2001 | Khazaka |
| 6,278,999 B1 | 8/2001 | Knapp |
| 6,293,284 B1 | 9/2001 | Rigg |
| 6,317,624 B1 | 11/2001 | Kollias et al. |
| 6,419,638 B1 | 7/2002 | Hay et al. |
| 6,436,127 B1 | 8/2002 | Anderson et al. |
| 6,437,856 B1 | 8/2002 | Jacques |
| 6,441,854 B2 | 8/2002 | Fellegara et al. |
| 6,507,747 B1 | 1/2003 | Gowda et al. |
| 6,510,366 B1 | 1/2003 | Murray et al. |
| 6,597,392 B1 | 7/2003 | Jenkins et al. |
| 6,600,947 B2 | 7/2003 | Averback et al. |
| 6,603,552 B1 | 8/2003 | Cline et al. |
| 6,619,860 B1 * | 9/2003 | Simon ........................ 382/112 |
| 6,624,843 B2 * | 9/2003 | Lennon ........................ 348/61 |
| 6,711,426 B2 | 3/2004 | Benaron et al. |
| 6,728,560 B2 | 4/2004 | Kollias et al. |
| 7,004,599 B2 | 2/2006 | Mullani |
| 7,015,929 B2 | 3/2006 | Satomi et al. |
| D564,663 S | 3/2008 | Udagawa et al. |
| 2001/0013897 A1 | 8/2001 | Kowno et al. |
| 2002/0059030 A1 | 5/2002 | Otworth et al. |
| 2002/0065468 A1 | 5/2002 | Utzinger et al. |
| 2002/0071246 A1 | 6/2002 | Stewart |
| 2002/0093698 A1 | 7/2002 | Kagawa |
| 2002/0133080 A1 | 9/2002 | Apruzzese et al. |
| 2002/0161664 A1 | 10/2002 | Shaya et al. |
| 2002/0177778 A1 | 11/2002 | Averback et al. |
| 2002/0181752 A1 * | 12/2002 | Wallo et al. ................ 382/128 |
| 2002/0182235 A1 | 12/2002 | Slavtcheff et al. |
| 2003/0007071 A1 * | 1/2003 | Goto .......................... 348/77 |
| 2003/0045916 A1 | 3/2003 | Anderson et al. |
| 2003/0067545 A1 | 4/2003 | Giorn et al. |
| 2003/0086703 A1 | 5/2003 | Kollias et al. |
| 2003/0086712 A1 | 5/2003 | Merola et al. |
| 2003/0108542 A1 | 6/2003 | Pruche et al. |
| 2003/0138249 A1 | 7/2003 | Merola et al. |
| 2003/0191379 A1 | 10/2003 | Benaron et al. |
| 2004/0006553 A1 | 1/2004 | de Vries et al. |
| 2004/0020509 A1 | 2/2004 | Waisman |
| 2004/0077951 A1 | 4/2004 | Lin et al. |
| 2004/0125996 A1 | 7/2004 | Eddowes et al. |
| 2004/0136701 A1 * | 7/2004 | Nakanishi et al. ............... 396/2 |
| 2004/0146290 A1 | 7/2004 | Kollias et al. |
| 2004/0174525 A1 | 9/2004 | Mullani |
| 2004/0186363 A1 | 9/2004 | Smit et al. |
| 2004/0263880 A1 | 12/2004 | Ito et al. |
| 2005/0116039 A1 | 6/2005 | Zhu et al. |
| 2005/0129288 A1 | 6/2005 | Chen et al. |
| 2005/0131304 A1 | 6/2005 | Stamatas et al. |
| 2005/0146863 A1 | 7/2005 | Mullani |
| 2005/0195316 A1 * | 9/2005 | Kollias et al. ................ 348/370 |
| 2006/0092315 A1 | 5/2006 | Payonk et al. |
| 2007/0002479 A1 | 1/2007 | Menke et al. |
| 2007/0004972 A1 | 1/2007 | Cole et al. |
| 2007/0005393 A1 | 1/2007 | Cole et al. |

FOREIGN PATENT DOCUMENTS

| | | |
|---|---|---|
| EP | 0737932 | 10/1996 |
| EP | 1089208 | 4/2001 |
| EP | 1118845 | 7/2001 |
| EP | 1194898 | 3/2003 |
| EP | 1297782 | 4/2003 |
| EP | 1376444 | 1/2004 |
| EP | 1433418 | 6/2004 |
| EP | 1434156 | 6/2004 |
| EP | 1541084 | 6/2005 |
| FR | 282 1152 | 8/2002 |
| FR | 208 314 | 4/2003 |
| GB | 2106241 | 4/1983 |
| GB | 2293648 | 4/1996 |
| JP | 7075629 | 3/1995 |
| JP | 7323014 | 12/1995 |
| WO | WO 94/24936 | 11/1994 |
| WO | WO 96/16698 | 6/1996 |
| WO | WO 97/05473 | 2/1997 |
| WO | WO 97/47235 | 12/1997 |
| WO | WO 98/24360 | 6/1998 |
| WO | WO 98/37811 | 9/1998 |
| WO | WO 99/17668 | 4/1999 |
| WO | WO 00/76398 | 12/2000 |
| WO | WO 01/04839 | 1/2001 |
| WO | WO 01/22741 | 3/2001 |
| WO | WO 01/22869 | 4/2001 |
| WO | WO 01/35827 | 5/2001 |
| WO | WO 01/45557 | 6/2001 |
| WO | WO 01/72216 | 10/2001 |
| WO | WO 01/82786 | 11/2001 |
| WO | WO 02/061405 | 8/2002 |
| WO | WO 03/040878 | 5/2003 |

OTHER PUBLICATIONS

"Calibration Apparatus and Method for Fluorescent Imaging", U.S. Appl. No. 11/863,345, filed Sep. 28, 2007, Inventors: Jeffrey Pote, et al.

"Apparatus and Method for Analyzing Skin Using L*a*b* Colorspace", U.S. Appl. No. 11/863,333, filed Sep. 28, 2007, Inventors: Gregory Payonk, et al.

"Method and Apparatus for Identifying Facial Regions", U.S. Appl. No. 11/863,323, filed Sep. 28, 2007, Inventors: Gregory Payonk, et al.

European Search Report EP 06/253372.

PCT Search Report PCT/US 02/35668.

European Search Report EP 06 25 3364.

European Search Report EP 06 25 3363.

Kollias, et al., "Fluorescence Photography in the Evaluation of Hyperpigmentation in Photodamaged Skin", Journal of the American Academy of Dermatology, vol. 36, No. 2, Part 1, 1997, pp. 226-230.

Muccini, et al., "Polarized Light Photography in the Evaluation of Photoaging", Journal of the American Academy of Dermatology, vol. 33, Nov. 1995, pp. 765-769.

Anderson, "Polarized Light Examination and Photography of the Skin", Arch Dermatol, vol. 127, Jul. 1991, pp. 1000-1005.

Kollias, et al., "Optical Non-Invasive Approaches to Diagnosis of Skin Diseases", Optical Diagnostics in Dermatology, vol. 7, No. 1, Dec. 2002, pp. 64-75.

Kligman, et al., "Ultraviolet ,Photography Serves as Both Predictor and Educator", Cosmetic Dermatology, vol. 10, No. 9, Sep. 1997, pp. 31-33.

Kollias, "Polarized Light Photography of Human Skin", Bioengineering of the Skin: Skin Surface Imaging and Analysis, Chapter 7, 1997, pp. 95-104.

Gartstein, et al., "Assessment of Visual Signs of Skin Aging", Bioengineering of the Skin: Skin Surface Imaging and Analysis, Chapter 3, 1997, pp. 331-345.

Doukas, et al., "Fluorescence Excitation Spectroscopy for the Measurement of Epidermal Proliferation", Photochemistry and Photobiology, 74(1), 2001, pp. 96-102.

Barel, et al., "The Visi-Chroma VC-100®; A New Imaging Colorimeter for Dermatocosmetic Research", Skin Research and Technology, 7, 2001, pp. 24-31.

Hillebrand, et al., "Quantitative Evaluation of Skin Condition in an Epidemiological Survey of Females Living in Northern Versus Southern Japan", Journal of Dermatologic Science, vol. 27, Supp. 1, 2001, pp. S42-S52.

Pagnoni, et al., "Digital Fluorescence Photography Can Access the Suppressive Effect of Benzoly Peroxide on Propionibacterium Acnes", Journal of the American Academy of Dermatology, vol. 41, No. 5, Part 1, 1999, pp. 710-716.

Lucchina, et al. "Fluorescence Photography in the Evaluation of Acne", Journal of the American Academy of Dermatology, vol. 35, No. 1, 1996, pp. 58-63.

Phillips, et al., "Polarized Light Photography Enhances Visualization of Inflammatory Lesions of Acne Vulgaris", Journal of the American Academy of Dermatology, vol. 37, No. 6, 1997, pp. 948-952.

Stamatas, et al., "Non-Invasive Measurements of Skin Pigmentation in Situ", Pigment Cells Res. 17, 2004, pp. 618-626.

Kollias, et al., "Fluorescence Spectroscopy of Skin", Vibrational Spectroscopy 28, 2002, pp. 17-23.

Zonios, et al., "Skin Melanin, Hemoglobin, and Light Scattering Properties Can Be Quantitatively Assessed in Vivo Using Diffuse Reflectance Spectroscopy", The Journal of Investigative Dermatology, vol. 117, No. 6, Dec. 2001, pp. 1452-1457.

Stamatas, et al., "Blood Stasis Contributions to the Perception of Skin Pigmentation", Journal of Biomedical Optics, vol. 9, No. 2, Mar./Apr. 2004, pp. 315-322.

Gillies, "Fluorescence Excitation Spectroscopy Provides Information about Human Skin in Vivo", The Journal of Investigative Dermatology, vol. 115, No. 4, Oct. 2000, pp. 704-707.

Z. Deyl, et al., "A Fluorescent Compound in Collagen and Its Relation to the Age of the Animal", Exp. Geront., vol. 5, 1970, pp. 57-62.

Na, et al., "Autofluorescence of Human Skin is Age-Related After Correction for Skin Pigmentation and Redness", The Journal of Investigative Dermatology, vol. 116, No. 4, Apr. 2001, pp. 536-540.

Leffel, et al., "In Vivo Fluorescence of Human Skin", Arch Dermatol, vol. 124, Oct. 1998, pp. 1514-1518.

Anderson, "Correspondence: In Vivo Fluorescence of Human Skin", Arch Dermatol, vol. 125, Jul. 1989, pp. 999-1000.

Odetti, et al., "Age-Related Increase of Collagen Fluorescence in Human Subcutaneous Tissue", Department of Internal Medicine and the Department of Physics, University of Genova, Italy, 1992, pp. 655-658.

Sandby-Moller, et al., "Skin Autofluorescence as a Biological UVR Dosimeter", Photodermatol Photoimmunol Photomed, 2004, pp. 33-40.

Kollias, et al., "Endogenous Skin Fluorescence Includes Bands That May Serve as Quantitative Markers of Aging and Photoaging", The Society for Investigative Dermatology, Inc., vol. 111, No. 5, Nov. 1998, pp. 776-780.

Brancaleon, "The In Vivo Fluorescence of Tryptophan Moieties in Human Skin Increases with UV Exposure and Is a Marker for Epidermal Proliferation", The Society for Investigative Dermatology, Inc., vol. 113, No. 6, Dec. 1999, pp. 977-982.

Tain, et al., "Aging and Effects of Ultraviolet a Exposure May Be Quantified by Fluorescence Excitation Spectroscopy In Vivo", The Society for Investigative Dermatology, Inc., vol. 116, No. 6, Jun. 2001, pp. 840-845.

Intl. Search Report from Intl. Appln. No. PCT/US 07/80032.

Intl. Search Report from Intl. Appln. No. PCT/US 07/80034.

Excerpt from website: www.ncbi.nlm.hih.gov, Bernstein et al., "Long term exposure alters the collagen of the papillary dermis. Comparison of sun protected and photoaged skin by northern analysis, immunohistochemical stainin, and confocal laser scanning microscopy," J Am Acad Dermatol., excerpt dated Feb. 1996, printed from the Internet Sep. 12, 2006 (3 pages).

Excerpt from website: www.ncbi.nlm.nih.gov, Richard et al., "Noninvasive measurement of the effect of lifetime exposure to the sun on the aged skin," Photodermatol Photoimmunol Phtotmed, excerpt dated Aug. 1994; printed from the Internet Sep. 12, 2006 (2 pages).

Excerpt from website: www.courage-khazaka.de, "Scientific Devices," printed from the Internet Feb. 16, 2005 (4 pages).

Excerpt from website: www.novatechcorp.com, printed from Internet Feb. 16, 2005 (1 page).

Courage + Khazaka electronic GmbH, "Studies List Reviscometer," Feb. 2003 (2 pages).

Excerpt from website: www.canfieldsci.com , "Imaging Systems," bearing copyright notice date of 2006, printed from the Internet Apr. 27, 2007 (5 pages).

Poyton, "A Technical Introduction to Digital Video", Color Science 1996 (J. Wiley & Sons), Chapter 7, pp. 115-154 (40 pages).

* cited by examiner

IMAGING APPARATUS AND METHODS FOR CAPTURING AND ANALYZING DIGITAL IMAGES OF THE SKIN

CROSS-REFERENCE TO RELATED APPLICATIONS

This application claims the benefit of U.S. Provisional Patent Application Ser. No. 60/848,765 filed Oct. 2, 2006, the disclosure of which is incorporated herein by reference in its entirety.

FIELD OF THE INVENTION

The present invention relates to apparatus and methods for assessing and analyzing the skin and more particularly to digital imaging and analysis of digital photographs taken of a subject. The analysis may be quantitative and comparative relative to another photograph of the same subject taken at another time or relative to a photograph or photographs taken of another person or persons.

BACKGROUND OF THE INVENTION

Various imaging systems have been proposed that photographically capture images of a person's face for analysis of the health and aesthetic appearance of the skin. Different images, captured at different times or under different lighting conditions can be used and/or compared to one another to gain insight into the condition of the skin and its response to treatment. This was typically done by human operators inspecting the photographs to identify certain visual indicators of skin condition and to ascertain changes between photographs. It would be beneficial for imaging systems to be less reliant on human perception and manual input. For example, in analyzing the skin, e.g., of a person's face, it is beneficial to examine specific regions of the face for specific associated attributes, since the different regions of the face are specialized in form and function and interact with the environment differently. Some skin imaging systems utilize a trained human operator to identify facial regions by manually touching (a stylus to a touch-sensitive input/output screen) or pointing to (with a cursor and clicking or otherwise indicating) fiducial points on a displayed facial image or drawing (with a stylus or cursor/mouse) polygons on an image to identify the facial regions of interest. While effective, such manual operations are labor intensive and require trained operators. It would therefore be beneficial for imaging systems to identify facial regions on images automatically to increase the speed and consistency of identification of the facial regions and to decrease the reliance upon operator input.

While the science of digital skin imaging analysis has identified various skin responses that are useful indicators of various skin condition parameters, it would still be desirable to identify and use additional specific responses of the skin that are indicative of skin condition. For example, it would be beneficial to identify skin imaging techniques that indicate photodamage and that reliably quantify and measure such indicative skin response. One of the indicators of skin condition is color response. Skin color is also important relative to the selection and design of cosmetics. There are limitations inherent in the expression of color in terms of RGB pixel intensity. It would therefore be beneficial to improve current methods of assessing skin color/brightness, e.g., for assessing skin condition and/or for the selection of and design of skin products, such as cosmetics.

Since imaging is a technical activity using complex apparatus, it remains an objective to improve the user-friendliness of digital imaging and analysis apparatus and to promote the ease and effectiveness of a digital imaging session, as well as enhancing the interaction between therapists/clinicians and patients/clients undergoing digital imaging sessions.

SUMMARY OF THE INVENTION

The disadvantages and limitations of known apparatus and methods for skin imaging and analysis are overcome by the present invention, which includes an imaging station for capturing images of a subject in a given ambient lighting environment. The imaging station has a housing with an aperture where the subject is presented for capturing images of the subject, a digital image capture device, a light for illuminating the subject during image capture, and a computer for controlling the image capture device and the light. The housing contains the digital image capture device, and the light and at least partially limits ambient light, if present in the ambient lighting environment, when a digital image of the subject is captured. In one embodiment of the present invention, the imaging station has the capability of taking a plurality of digital images of a subject under a plurality of illuminating conditions, storing, displaying and analyzing the digital images.

DETAILED DESCRIPTION OF THE INVENTION

Figure 1:
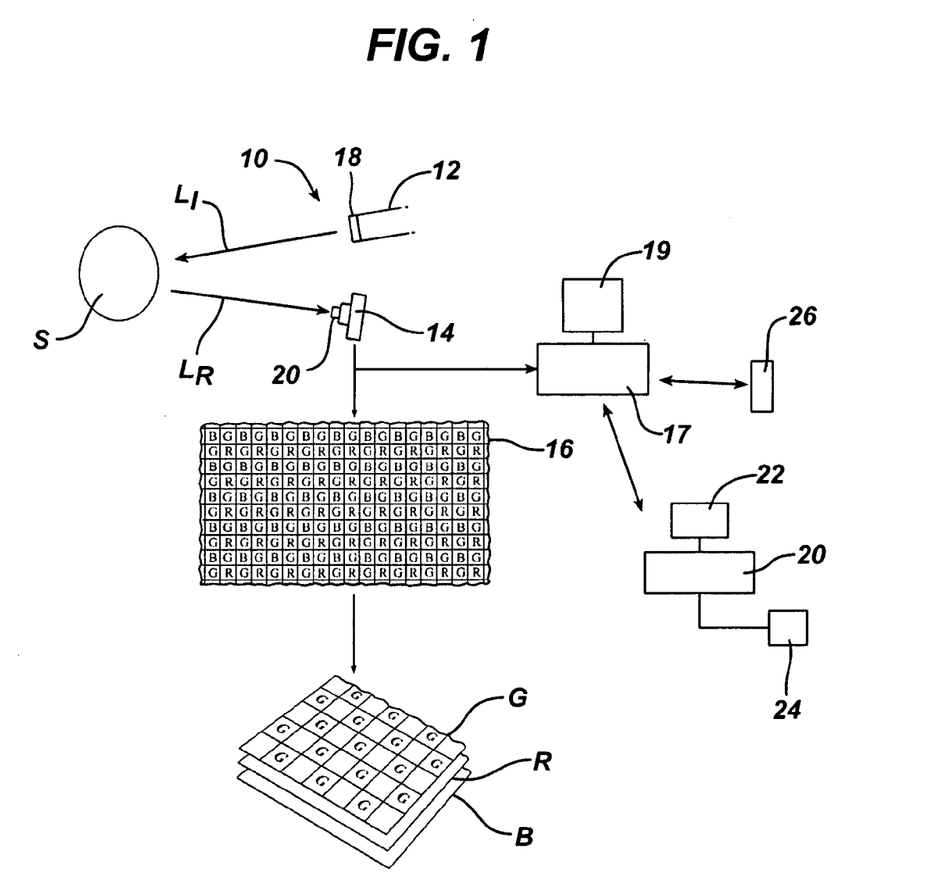
FIG. 1 is a diagrammatic view of a digital imaging system in accordance with the present invention.

FIG. 1 diagrammatically illustrates a digital imaging apparatus 10 having a source of illuminating light 12 (e.g., a photo flash) and a digital camera 14. An image of the subject S is recorded by the camera 14 in the form of a matrix 16 of pixel values in RGB format (red, green, blue). The matrix 16 of values is typically produced by a Bayer-filtered close-coupled display (CCD) and the information is stored in a memory device, such as random access memory (RAM) of computer 17 or on a flash memory card. The RGB data can be separated into channels or planes, R, G and B, one plane for each color. Various frequencies of illuminating light $L_I$ disposed at varying positions relative to the subject S may be used to capture digital images of the subject S in order to capture different information about the skin of the subject. Filters 18, 20 may be employed on the light 12 and the camera 14, respectively, to control the light frequency/polarity of light $L_I$ which is projected on the subject S, as well as controlling the light $L_R$ (reflected or emitted from the subject S), which is admitted into the camera 14. Imaging of this type is described at length in U.S. patent application Ser. No. 10/008,753, entitled, "Method of Taking Images of the Skin Using Blue Light and the Use Thereof", which was published as Pub. No. US 2004/0146290 A1, U.S. patent application Ser. No. 10/978,284, entitled, "Apparatus for and Method of Taking and Viewing Images of the Skin", which was published as Pub. No. 2005/0195316 A1 and U.S. patent application Ser. No. 11/169,813, entitled, "Skin Imaging System with Probe", which was published as Pub. No. US 2006/0092315 A1, all of which are incorporated in their entirety by reference herein and which are appended hereto as Appendices 1-3. Unless specifically described otherwise, the present invention as described herein in reference to FIGS. 1-4 has the features and functionality disclosed in the foregoing U.S. patent applications. The foregoing applications disclose various correlations between skin condition and the images produced by various photographic parameters, i.e., specific combinations of illuminating light $L_f$, filters 18, 20, etc. The skin response to different illuminating frequencies, angles, polarity, etc. can reveal information about skin condition and this evidence of skin condition can be recorded and recalled in digital images for purposes of analysis.

Since the images recorded are in digital form, i.e., in numerical pixel intensity values, the images lend themselves to quantitative analysis, such as by a program or programs residing on computer 17. For example, instead of just noting that the cheek of a subject whose image is taken at time $T_1$ is more or less red in color in an image of the person taken at time $T_2$, as discerned by a skilled human observer, the values of the intensity of the red pixels in the specific area of the cheek at times $T_1$ and $T_2$ may be quantitatively compared. For example, the two values may be mathematically processed to determine the actual change in red intensity for that pixel. Digital image quantification can be used to discern average values for the skin in specified regions, e.g., by summing the values of pixels in the specific region of interest and then dividing by the number of pixels. In this manner, a whole area of skin, e.g., of the face, may be characterized quantitatively. Various other quantified analyses may be conducted, e.g., the imaged area of skin may be tested for standard deviation in pixel intensity.

The present invention recognizes that digital imaging apparatus 10 may include communications apparatus such as modems, e.g., cable and DSL modems, to communicate digital image data and related communications from a digital imaging computer 17 to a remote computer 20 that may be in the home or workplace of an interested person, such as a fellow clinician, cosmetologist, a patient or a cosmetics customer. The receiver can then review the image data and other related communication on the monitor 22 of their computer 20. These communications may be conducted over the Internet using wired or wireless connections. In addition to sending image data to others, the imaging apparatus 10 may also receive image and related data from others, such as fellow clinicians, patients, etc. via the same means of communication. For example, a cosmetics customer may capture their own image with a local CCD camera 24 and relay that image to the imaging system computer 17 via the Internet, e.g., as an e mail attachment. The image may be examined and a responsive communication prepared by a cosmetologist and sent to the customer. The responsive communication may contain images, e.g., past images taken of the customer that are relevant to the customer, images relevant to cosmetics, etc. These can be sent as attachments to an e mail message. The present invention also recognizes that a cell phone 26 may be used to capture and communicate image information and related communications between parties at the imaging station 10 and parties remote therefrom.

Figure 2:
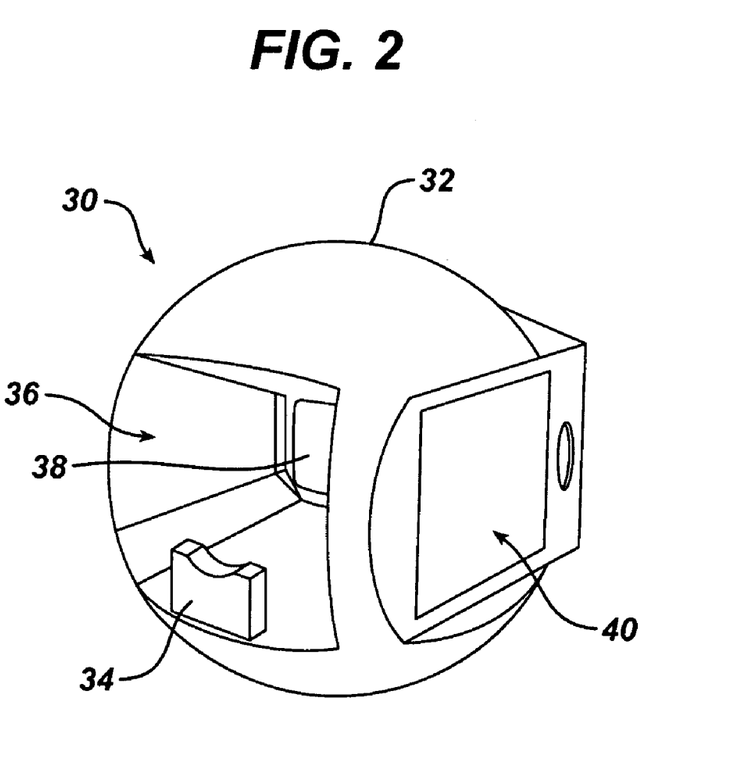
FIG. 2 is a perspective view of an image capturing apparatus in accordance with an embodiment of the present invention.

FIG. 2 shows an imaging station 30 having a generally spherical outer housing 32. The housing 32 may be supported on a flat surface such as a counter or table or be provided with a rotatable mounting, as would be known to one of normal skill in the art. A chin rest 34 is positioned at the open end of a tunnel or "funnel" 36, which extends into the interior of the housing 32. At the other end of the tunnel 36 opposite to chin rest 34, a self-visualizing panel 38, such as a mirror or alternatively, a display, such as a flat panel display, allows a user of the imaging station 30 to see themselves when they are positioned with their chin on the chin rest 34. An operator display 40 on the exterior surface of the housing 32 allows an operator, such as a dermatologist, clinician or cosmetologist to view digital images, e.g., those taken of a subject who uses the imaging station 30. The operator display 40 may be a touch-screen display to function as an operator interface whereby the operator can provide input to the imaging station, e.g., in the form of commands, data, menu selections, or graphic entry by way of drawing on the display 40 with a stylus. After digital images have been captured, the operator display 40 may be used to display the images captured to the operator and to the subject person who can simultaneously view and discuss the images and what is shown in them.

Figure 3:
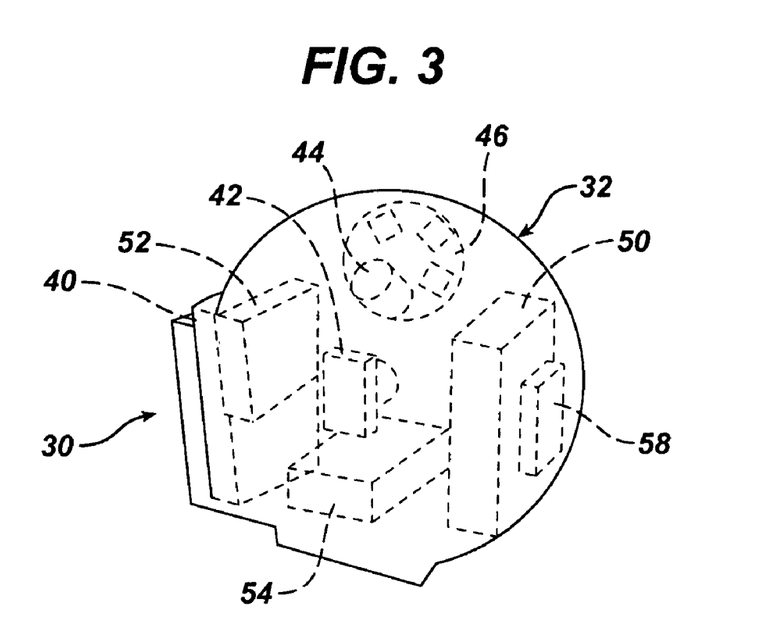
FIGS. 3 and 4 are phantom views of the imaging apparatus of FIG. 1 looking from the back and side, respectively.
Figure 4:
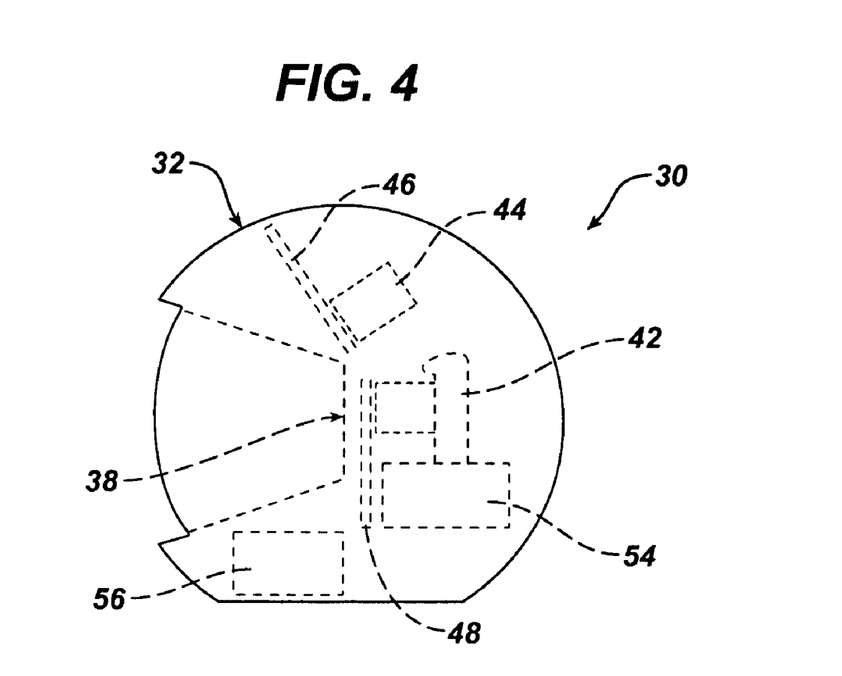

FIGS. 3 and 4 show that the imaging station 30 has a digital camera 42 positioned proximate the self visualizing panel 38 for capturing digital images of a subject person (user of the imaging station). A light 44, such as a strobe light or other photo flash is positioned proximate to the camera 42 for illuminating the subject when photos are taken. Filter wheels 46, 48 with associated positioning motors and position sensors (not shown) filter the light emitted from the light 44 and entering the camera 42, respectively. The light 44, camera 42 and/or associated filter wheels 46, 48, may all be moveable to achieve different orientations for imaging. Computer 50, e.g., a personal computer (PC), controls the imaging session, providing instructions to the operator through a speaker and/or on the operator display 40 and receiving input from the operator, powering and triggering the light 44, the filter wheels 46, 48 and the camera 42. The digital images are stored in the camera 42 and by the computer 50 on at least one storage device, such as in RAM and/or on a DVD recorder 52. The housing also contains other necessary peripherals, such as strobe power pack 54, a power supply 56 for the computer 50 and a power supply 58 for the operator display 40. The positioning of the various components of the imaging station 30 are determined by their physical packing and accommodation into the housing 34 and may be repositioned as needed depending upon their specific exterior dimensions.

Figure 5:
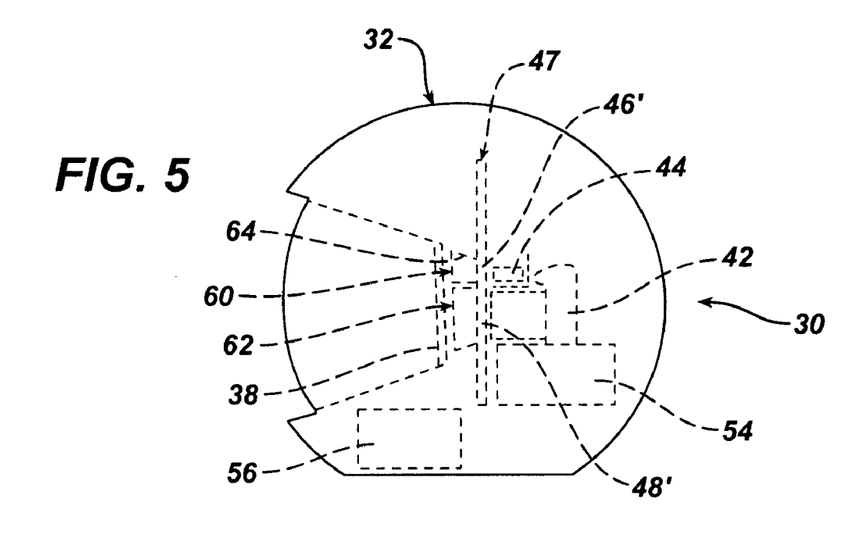
FIG. 5 is a phantom view like FIGS. 3 and 4 but showing an alternative embodiment of the present invention.
Figure 6:
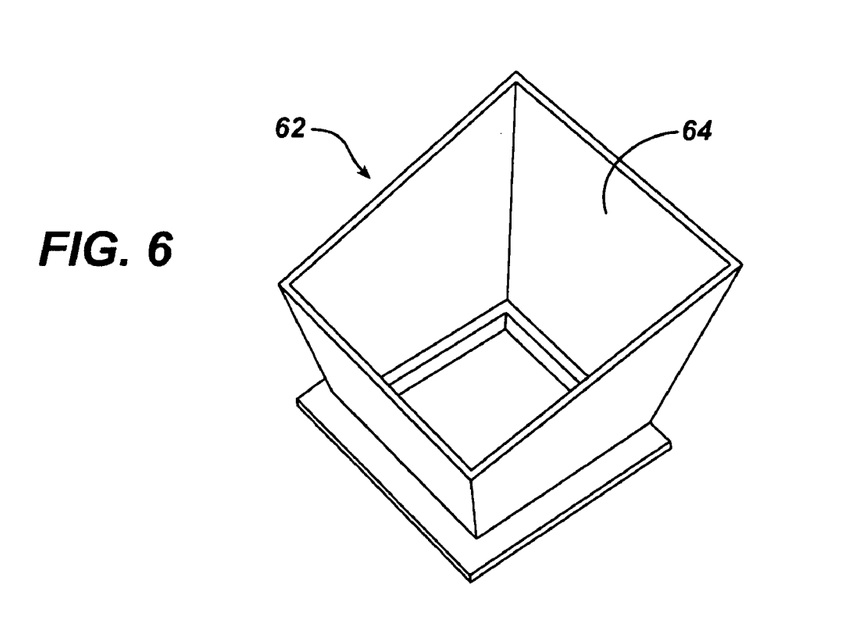
FIG. 6 is a perspective view of a light guide in accordance with an embodiment of the present invention.

In documenting and assessing skin from cosmetic and health perspectives, the better controlled the light properties (e.g., reflection, scattering, polarization, excitation wavelength and excitation bands), the better the resulting data and analysis of the skin. FIGS. 5 and 6 show light guides 60 and 62, which can be used to control light emitted from light 44 and captured by camera 42, respectively. This is because the light leaving a light source (i.e. strobe) will naturally begin to scatter and disperse. Light guide 60 helps to maintain the proper optical properties in order to illuminate a face or other object in order to minimize any interference from surfaces, de-polarization of light or fluorescence of materials (objects or surfaces) other than the analyzed face or object which would cause the light to produce poor quality images. In addition, scatter light captured by camera 42 may interfere with the sharpness of the image. Light guide 62 helps to eliminate the scatter light. The light guides 60, 62 may be formed of one or more flat or curved surfaces placed in front of the light 44 and camera 42, respectively. The light guides 60, 62 may be formed into a square, flare, conical, frustoconical, or round shape hood. Preferably, the color and texture of the interior surfaces 64 of the light guides 60, 62 absorb light, e.g., painted or made of flat black color. The color and/or texture of outside surfaces should not affect the quality of image captured by the camera 42. It should be understood that the light guides 60, 62 depicted in FIG. 4 could be recessed further into the housing 32 by moving the light 44 and the camera 42 deeper into the housing 32, e.g., behind screen 38. As a result, the light guides 60, 62 can be hidden within the housing 32. As shown in FIG. 5, the filters 46', 48' can be disposed on a common wheel 47.

The imaging station 32 may be provided with all the image capture and processing apparatus as described in Publication Nos. 2004/0146290, 2005/0195316 and 2006/0092315, which is contained within the housing 32. The imaging station preferably has the capability to rotate at least 90 degrees, e.g., either on a supporting surface or rotatable platform and/or to rotate up and down and/or lift or drop in height to accommodate users of various height and seated on various seating arrangements. The tunnel 36 in conjunction with the chin rest 34 and self visualizing panel 38, cooperate to position the subject person in a maximal position (relative to the light 44 and camera 42) for imaging the face of the subject person. The tunnel 36 also reduces the intrusion of environmental lighting during imaging sessions, limits the light projected into the environment when the light 44 is operated during an imaging session and provides the subject person with privacy. The operator display 40 may be used to visualize the subject person, before, during and after imaging, i.e., the camera 42 may be operated in real-time/video mode to show the moving image of the subject person as they place themselves on the chin rest 34 and otherwise prepare to undergo imaging (close their eyes etc.) This real time feed may be used to display the subject on the operator display 40, as well as on the self visualizing panel 38 (display). In this manner, the operator display 40 may be used to display the view that the camera 42 "sees". As shown, e.g., in Publication No. 2005/0195316 A1, the camera 45 and illuminating light or lights 44 would be positioned adjacent to the self visualizing panel 38. In the case of a mirror-type self visualizing panel, the mirror material may be partially or entirely made of "one-way" glass or a half-mirror. Of course, if the functionality of subject self-visualization is not needed or desired, e.g., in the context of an imaging station 30, which is not intended for subject control or one which relies on verbal commands to the subject and does not need visual cues to the subject, the self-visualizing panel 38 may be omitted or replaced with a clear panel, such as clear glass or plastic. With respect to insuring that the subject person has their eyes closed, the operator display 40 may be used to apprise the operator of this condition, so the operator may then know it is safe to trigger imaging, e.g., by depressing a virtual button on the operator display 40.

The computer 50 is preferably provided with a plurality of data ports, e.g., USB and or Ethernet ports and/or 1394 "firewire", wireless capacity or other interface standards for sharing the data captured by the imaging station 30 with other computers, e.g., on a network like the Internet, and for receiving data from other computers for display on the imaging station 30, e.g., imaging data from population studies, skin care product information, etc. A printer (not shown) may also be used in conjunction with the imaging station 30 to print out images, advice and/or information concerning the skin condition and treatment of the subject person.

As described in a commonly owned patent application entitled, Method and Apparatus for Identifying Facial Regions, which was filed on Oct. 2, 2006 as Provisional Application No. 60/848,741 and which is incorporated in its entirety herein, quantitative analysis of skin condition can be facilitated and improved by identifying specific regions of the skin, e.g., of the face. This identification of regions of interest can be conducted automatically through pupil or flash glint identification as fiducial reference points for mapping the facial regions.

As described in a commonly owned patent application entitled, Apparatus and Method for Analyzing Skin Using L*a*b* Colorspace, which was filed on Oct. 2, 2006 as Provisional Application No. 60/848,768 and which is incorporated in its entirety herein, identification of skin photo-response indicative of skin condition, quantitative analysis of skin condition, color and brightness can be facilitated and improved by converting digital image data from RGB format to L*a*b* format. As described in Application No. 60/848,768, the process for converting RGB image data to L*a*b* colorspace data is known to one of normal skill in the art, e.g., as described in Charles Poynton, A Technical Introduction to Digital Video (J. Wiley & Sons) Chapter 7, "Color Science." Application No. 60/848,768 also discloses that facial regions may be identified by an operator marking a displayed image with a cursor tool or by programmatically analyzing the image data to identify pixel values consistent with unique fiducial reference points, such as the pupils, which would have unique color (black or flash glint), shape (round), size, spacing and orientation. Once pupils are identified, facial regions may be calculated relative thereto in accordance with empirically determined spacial/dimensional relationships to the pupils. RGB to L*a*b* conversion may be used to aid in selecting cosmetics for an individual from a palette of available cosmetic colors or may be used to select/design hues of cosmetics in defining a color palette for use by a population.

As described in a commonly owned patent application entitled, Apparatus and Method for Measuring Photodamage to Skin, which was filed on Oct. 2, 2006 as Provisional Application No. 60/848,767 and which is incorporated in its entirety herein, the green response intensity of skin to illumination by blue light can be used to identify and quantify photodamage to the skin, e.g., due to the presence of elastotic material. Further, a population's digital skin imaging data concerning photodamage and/or other skin conditions can be characterized numerically and analyzed statistically. Quantitative analysis of digital images of the skin response, such as the degree of variation of green signal response over a surface of the face as an indicator of photodamage, can be used to assess photodamage, and develop a number or score of skin condition relative to a population.

As described in a commonly owned patent application entitled, Calibration Apparatus and Method for Fluorescent Imaging, which was filed on Oct. 2, 2006 as Provisional Application No. 60/848,707 and which is incorporated in its entirety herein, a calibration standard may be employed during an imaging session, e.g., during blue fluorescent photography, to identify variations in illumination intensity between images taken at different times. Having identified a circumstance where illumination intensity has varied, the operator of the imaging apparatus can be notified to correct the conditions leading to illumination variations. Alternatively, the imaging apparatus may compensate for the variations by adjusting the intensity of the illuminating light or normalizing the images by digital image processing.

Each of the inventions disclosed in the foregoing applications incorporated by reference may be utilized and incorporated in the imaging station 30 of the present invention. In doing so, certain synergies are realized through their combination and interrelationship. For example, the capability of manually or automatically identifying facial regions has utility in the color ascertainment of certain facial regions, e.g., the cheek or the "average color" of the combination of cheek, forehead and chin. This capability of identifying skin color in certain regions can be helpful in matching cosmetics to those regions or combinations of those regions. For example, in selecting or designing colors for cosmetic foundations, it would be beneficial to know the average color of the facial regions: cheek, forehead and chin and exclude the lips, eyebrows and eyes from the contributing colors.

The identification of facial regions may also be used in the imaging station 30 in conjunction with the teachings of the application directed to ascertaining photodamage, in that specific regions of the skin are more prone to photodamage due to skin composition and exposure likelihood. The calibration of the apparatus and techniques taught in the application pertaining to same can be used in the imaging station 30 in that any set of digital images can be normalized to compensate for variations in illumination intensity as distinguished from variations in response intensity attributable to skin variation.

The imaging station 30, provides an apparatus and method of obtaining digital image data information concerning the appearance and light response characteristics of a person's skin. Since the present invention can be used by numerous persons, the data obtained from the use of the present invention, as well as data obtained from other sources, such as digital images made by others using different apparatus and methods, may be used to analyze the individual relative to others. As noted, e.g., in the Application entitled Apparatus and Method for Measuring Photodamage to Skin, which is incorporated by reference herein, digital images can be analyzed quantitatively to provide a discrete measurement of skin condition(s). An alternative, traditional method for assessing skin condition is through the judgment of a person based upon the appearance of the image. Over the years it has been shown that experienced clinicians can accurately and effectively discern changes in skin condition, based upon their visual perception, e.g., in comparing two images taken at two different times. Accordingly, the present invention recognizes the value of human perceptive judgments of skin condition in forming an accurate assessment of skin condition. This human perceptive measure can be used in parallel to quantitative, automated methods to confirm one with the other and thereby increase the credibility of both.

The present invention includes a method for training, implementing and testing visual analysis of images of subject persons. More particularly, to train persons to perceptively and accurately judge skin condition based upon images, training sets of images may be assembled. A training set may be a set of images taken of a person over time, which illustrates their skin condition over time. The image set can be divided into various categories, e.g. one category may be images taken with blue light and sensitive to green signal response of the skin to indicate photodamage. The image sets can then be reviewed by one or more person who are trained professionals with a proven proficiency in ascertaining skin condition based upon review of images of the skin of subject persons. The proficient individual or individuals will then order the image set into a range of conditions extending from the worse condition to the best condition. This ordering can be conducted in conjunction with quantified analysis. For example, six images may be considered and arranged from best to worst illustrating the spectrum of skin condition exhibited by the subject person relative to photodamage. Having developed this reference set or training set of images, persons to be trained are taught the visual indicators to look for to discern photodamage. The trainees are then shown the training image set, e.g., two images at a time, randomly selected by a computer, and asked to characterize which of the two displayed images is better or worse, e.g., with respect to photodamage.

In presenting the images, the position of the better and worse images (either in the right or left, upper or lower positions on the display) is randomized, such that the display position does not correlate to the skin condition. After the trainees can successfully identify the better and worse images consistently, i.e., match the conclusions of a professional with demonstrated expertise, then the trainee can be adjudged to have assimilated the necessary perception to discern skin condition from digital images.

Assuming that a person is available with suitable training in judging skin condition, the same automated technique of presenting a plurality of images and receiving the judgment of better or worse can be applied to the process of evaluating an individual's skin condition over time. For example, if a person has had a series of imaging sessions, e.g., ten sessions over a period of two years, then a clinician can be automatically and randomly presented with a series of images taken from these imaging sessions and categorize them as better or worse than another image displayed. This process can be repeated until an unbiased repeating pattern of relative ranking is clearly established, demonstrating a reproducible clinical judgment. From this judgment, the subject person can be advised as to when their skin exhibited its best condition, the worse condition, the pattern of improvement or worsening, etc. This type of analysis can be applied to measure the success or failure of treatment and can be used in conjunction with quantitative methods to provide a balanced, informed analysis.

The foregoing methods for training and/or clinically assessing skin condition can be conducted on the imaging station 30. For example, after an imaging session, the clinician can perform a clinical assessment witnessed by the subject person.

It should be understood that the embodiments described herein are merely exemplary, and that a person skilled in the art may make many variations and modifications without departing from the spirit and scope of the invention. All such variations and modifications are intended to be included within the scope of the invention.

We claim:

1. An imaging station for capturing images of a subject in a given ambient lighting environment, comprising:
   a housing with an aperture where the subject is presented for capturing images thereof;
   a camera for capturing digital images;
   a light for illuminating the subject during image capture;
   a first display visible to a user and disposed in the housing for displaying a digital image of the subject captured by said camera and permitting the subject to see themselves as they appear when presented to said aperture;
   a second display visible on the exterior of the housing for displaying a digital image of the subject captured by said camera, said second display presenting an operational interface through which the imaging station may be controlled;
   a computer for controlling the camera, said first and second displays and the light, said housing containing the camera and the light and including a tunnel extending from said aperture toward said camera and said light, said tunnel at least partially limiting ambient light, if present in the ambient lighting environment, when a digital image of the subject is captured and when viewing images on the first display.

2. The imaging station of claim 1, wherein said second display is mounted on a side of said housing generally parallel to and beside said tunnel.

3. The imaging station of claim 2, further comprising a first moveable filter for effecting the light emitted by the light for illuminating the subject, such that a plurality of different types of images may be captured with the imaging station.

4. The imaging station of claim 3, wherein said first moveable filter is disposed on a filter wheel within the housing, rotatable before said light to assume at least two positions, a first position filtering light from said light and a second position not filtering light from said light.

5. The imaging station of claim 4, further comprising a second moveable filter having a plurality of positions relative to said camera, a first position filtering light entering said camera and a second position not filtering light entering said camera.

6. The imaging station of claim 5, wherein the first and second moveable filters are disposed on a common filter wheel.

7. The imaging station of claim 1, wherein said housing has a chin rest disposed proximate said aperture for receiving a chin of the subject, said housing being adjustable in position relative to a subject to position the subject's chin on said chin rest.

8. The imaging station of claim 1, further comprising a light guide for guiding at least one of light emitted from said light and light directed toward said camera from the subject.

9. The imaging station of claim 8, wherein said light guide has a tunnel shape with an aperture at either end and a lumen passing therebetween.

10. The imaging station of claim 1, wherein said computer is programmed to identify a plurality of facial regions and to convert RGB colorspace images captured by the imaging station to L*a*b* colorspace values to facilitate image processing and quantitative analysis.

11. An imaging station in accordance with claim 1, further comprising:

a plurality of said imaging stations coupled to a network, said network allowing the communication of images to selected ones of said imaging stations.

12. The imaging station of claim 11, wherein an image may be communicated to a selected imaging station as an e mail attachment.

13. The imaging station of claim 11, wherein a cell phone image may be communicated to a selected imaging station through said network.

14. An imaging system, comprising:

a plurality of imaging stations capable of capturing and storing digital images of persons, each imaging station having a digital image capture device, an illuminating light, at least one filter for changing the illuminating light, such that a plurality of types of light are available for capturing a plurality of different types of digital images and a computer for controlling said image capture device, said filter and said illuminating light, said plurality of imaging stations coupled to a network, said network allowing the communication of images to selected ones of said imaging stations, wherein said computer is programmed to quantitatively analyze digital images, such that a plurality of digital images may be quantitatively ordered relative to each other based upon a given criteria exhibited by the plurality of digital images.

15. The imaging system station of claim 14, wherein said computer is programmed to present the plurality of digital images to a trainee to test the trainee's capacity to differentiate between condition states of skin as revealed by the plurality of digital images and to record the degree of success/failure exhibited by the trainee.

16. The imaging system of claim 15, wherein the plurality of images are presented in pairs and the trainee is asked to rank the pair of images as to a particular condition state.

* * * * *